(12) United States Patent
Shah et al.

(10) Patent No.: US 8,431,609 B2
(45) Date of Patent: Apr. 30, 2013

(54) PROCESS FOR PREPARATION OF PYRAZOLE DERIVATIVES

(76) Inventors: Darmesh Mahendrabhai Shah, Maharashtra (IN); Guruprasad Wader, Maharashtra (IN)

( * ) Notice: Subject to any disclaimer, the term of this patent is extended or adjusted under 35 U.S.C. 154(b) by 708 days.

(21) Appl. No.: 12/527,857

(22) PCT Filed: Apr. 30, 2007

(86) PCT No.: PCT/IN2007/000174
§ 371 (c)(1),
(2), (4) Date: Mar. 17, 2010

(87) PCT Pub. No.: WO2008/102367
PCT Pub. Date: Aug. 28, 2008

(65) Prior Publication Data
US 2010/0190988 A1     Jul. 29, 2010

(30) Foreign Application Priority Data
Feb. 19, 2007   (IN) .......................... 323/MUM/2007

(51) Int. Cl.
*A61K 31/415*    (2006.01)
*C07D 231/14*    (2006.01)

(52) U.S. Cl.
USPC ........................................ 514/406; 548/374.1

(58) Field of Classification Search ............... 548/374.1; 514/406
See application file for complete search history.

(56) References Cited

U.S. PATENT DOCUMENTS
5,462,960 A    10/1995   Barth
5,624,941 A    4/1997   Barth

FOREIGN PATENT DOCUMENTS

| | | | |
|---|---|---|---|
| CN | 1110968 A | | 11/1995 |
| CN | 1346349 A | | 4/2002 |
| EP | 0576357 A1 | * | 6/1993 |
| EP | 576357 A1 | | 12/1993 |
| EP | 656354 A1 | | 6/1995 |
| EP | 658546 A1 | | 6/1995 |
| WO | 2006021652 A1 | | 3/2006 |

* cited by examiner

*Primary Examiner* — Kamal Saeed
*Assistant Examiner* — Janet L Coppins
(74) *Attorney, Agent, or Firm* — Kramer & Amado, P.C.

(57) ABSTRACT

A process for preparation of Pyrazole derivatives adapted for one pot reaction involving the use of a pyclizing agent and involving the step of amidation in the presence of a catalyst. The steps for isolation and purification of found Pyrazole derivatives are also disclosed.

55 Claims, No Drawings

PROCESS FOR PREPARATION OF PYRAZOLE DERIVATIVES

FIELD OF INVENTION

This invention relates to a process for preparation of pharmaceutically useful substances.

More particularly the present invention relates to a process for preparation of pyrazole derivatives.

BACKGROUND
Definitions

As used in the present specification, the following words and phrases are generally intended to have the meanings as set forth below, except to the extent that the context in which they are used indicate otherwise.

The term "alkoxy" means alkyl group bonded with oxygen as a single group.

The term "Alkyl" as used in this specification includes $C_1$-$C_{12}$ members of the aliphatic homologous series.

The term "aryl" as used in this specification, includes, for example, phenyl optionally substituted by one or two substituents selected from nitro, halo, $C_1$-$C_4$ alkyl, $C_1$-$C_4$ alkoxy, hydroxy, trifluoromethyl, and cyano. It also includes 1- and 2-naphthyl.

The term "heteroaryl" as used in this specification includes, for example, benzofuranyl; benzothienyl; pyridyl optionally monosubstituted by methyl or cyano; quinolyl; benzoxazolyl; benzthiazolyl; furyl; pyrimidinyl; thiazolyl; and thienyl optionally monosubstituted by halo or $C_1$-$C_4$ alkyl.

"Halo" means fluoro, chloro, bromo or iodo.

"One Pot Reaction" in the context of this invention is a strategy to improve the efficiency of a chemical reaction whereby a reactant or set of reactants are subjected to successive chemical reactions in just one reaction vessel.

"Scavenging agent" means an agent that removes unwanted components.

"cyclization" means a process for formation of a ring.

Acronyms and Abbreviations Used in Specification:
"NMR" means Nuclear Magnetic Resonance.
"IR" means Infrared Spectroscopy.
"ppm" means parts per million.
EDC—ethylenedichloride
MDC—methylenedichloride
MTBE—methyl tert-butyl ether
GC—Gas chromatography
HPTLC—High-performance thin-layer chromatography
DMSO—Dimethyl sulfoxide
EDTA—ethylene diaminetetraacetic acid
EtOH—ethyl alcohol
HPLC—High performance liquid chromatography
HCl—Hydrochloric acid
IR—Infra red
TLC—Thin Layer Chromatography
TMSCL—Trimethylsilyl chloride
"XRD"—X-Ray Diffraction pattern.

INTRODUCTION

Pyrazole derivatives showing affinity for cannabinoid receptors are described in EP-A-576357, EP-A-658546 and EP-A-656354.

Various Pyrazole-3-carboxamide derivatives showing high affinity for cannabinoid receptors are disclosed in U.S. Pat. No. 5,462,960.

Also disclosed in the aforementioned US patent is a process for preparation of Pyrazole-3-carboxamide derivatives. In accordance with the aforesaid process, a functional derivative of the Pyrazole-3-carboxylic acid such as Pyrazole-3-carboxylic acid chloride is obtained by treating the Pyrazole-3-carboxylic acid with thionyl chloride.

Pyrazole-3-carboxylic acid chloride so obtained is then treated with an amine in the presence of a solvent such as dichloromethane in an inert atmosphere and in the presence of a base such as triethylamine. Similar processes for the preparation of Pyrazole-3-carboxamide derivatives are disclosed in U.S. Pat. No. 5,624,941 and EP0656354.

Scheme I and scheme II given herein below describe the reactions as disclosed in the aforementioned patents.

Reaction Scheme I

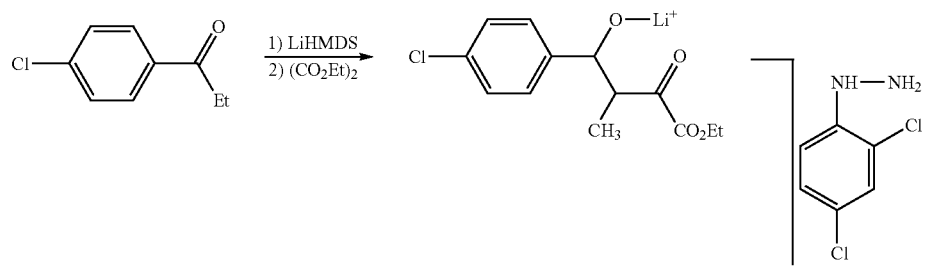

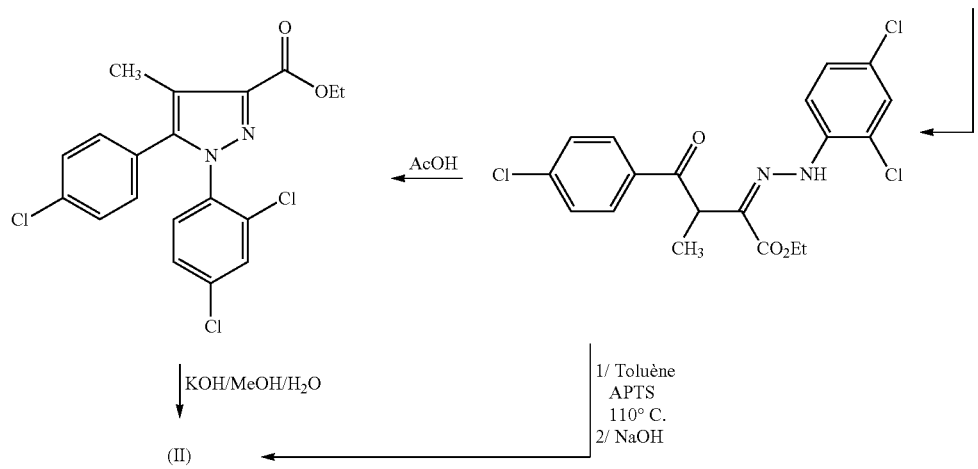
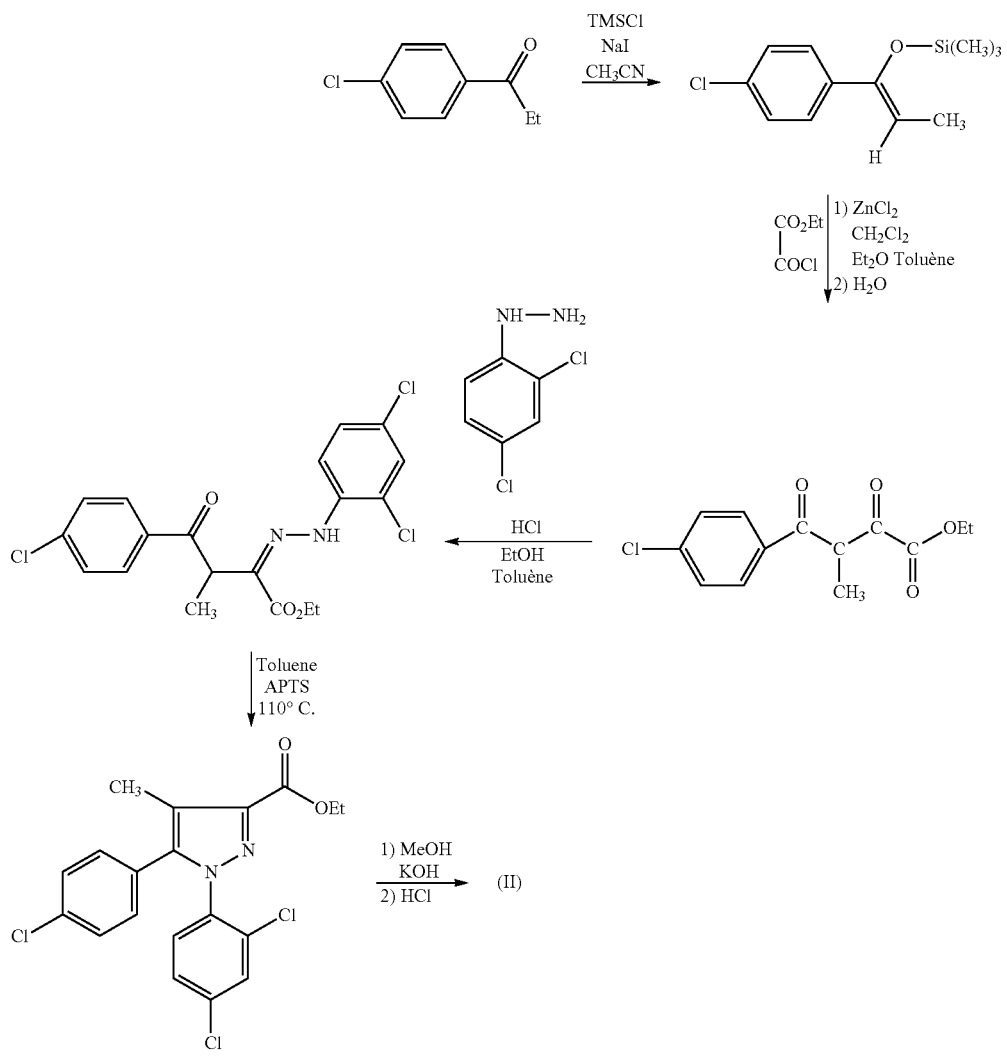
LiHMDS: lithium salt of hexamethyldisilazane,
PTSA: Paratoluenesulfonic acid
TMSCl: Chlorotrimethylsilane
PTSA: Paratoluenesulfonic acid Another process is disclosed in WO2006/021652 wherein Pyrazole-3-carboxylic acid is converted to a Pyrazole-3-hydrazide intermediate. Subsequently the Pyrazole-3-hydrazide intermediate is treated with a pentamethyl-dihalide to afford Pyrazole-3-carboxamide derivative namely rimonabant. However, this process uses toxic and expensive dihalo-pentamethyl derivatives and unsafe hydrazine hydrate. Furthermore, the product obtained via this process needs to be purified using column chromatography thereby adding to the complexity involved in isolation of the final product.

Known processes for preparation of pyrazole-3-carboxamide derivatives as described in Scheme I and Scheme II involve steps wherein intermediates have to be isolated and purified during the process thereby making the overall process lengthy and complicated. Particularly this may involve transferring at least some of the reactants into different vessels for variety of reaction steps during the process.

Thus known processes for preparation of pyrazole-3-carboxamides involve at least one or more method steps as given below:
  i. Isolation of pyrazole-3-carboxylic acid esters after synthesis,
  ii. hydrolysis of pyrazole-3-carboxylic acid esters,
  iii. subsequent isolation of pyrazole-3-carboxylic acid derivatives,
  iv. treatment of the isolated and dried pyrazole-3-carboxylic acid derivatives with highly toxic and unsafe chlorinating agents such as thionyl chloride, oxalyl chloride, phosphorous oxychloride and the like followed by, and
  v. isolation of unstable pyrazole-3-carboxylic acid chlorides for further reaction with substituted amines in presence of solvents and acid acceptors.

Therefore there is a need for a simple economical, faster process for preparation of pyazole-3-carboxamide derivatives.

OBJECTS OF INVENTION

It is an object of this invention to provide a process for preparation of Pyrazole-3-carboxamide derivatives, which is devoid of additional steps of isolating intermediate compounds during the reaction process thereby saving valuable process time, energy and the need for additional equipments and reagents.

Another object of this invention is to provide a simple process for, preparation of Pyrazole-3-carboxamide derivatives, wherein the necessary routine method steps employed in the conventional processes are completely obviated thereby making the overall process drastically simple, economical, eco-friendly, safe and faster.

Still another object of this invention is to provide a process for preparation of Pyrazole-3-carboxamide derivatives which does not involve the use of reagents like thionyl chloride thereby making the process eco-friendly and safe.

Still further object of this invention is to provide a process for preparation of Pyrazole-3-carboxamide derivatives wherein variety of synthons as amines can be introduced for preparation of diverse chemical entities.

SUMMARY OF INVENTION

To meet the aforementioned objectives there is provided in accordance with this invention a process for preparation of compounds of Formula IV comprising the following method steps:

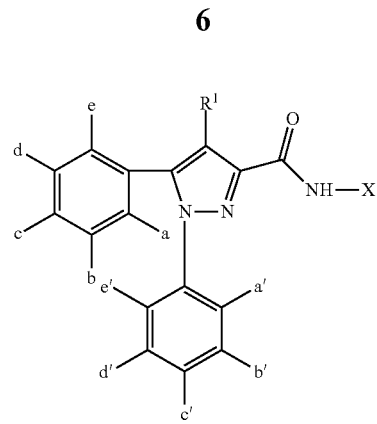

IV wherein, a, b, c, e, and a' b' c' d' e' are identical or different and are independently hydrogen, a halogen, a $(C_1-C_{12})$ alkyl, a $(C_1-C_{12})$ alkoxy, a trifluoromethyl, a nitro group, nitroaryl, nitroalkyl and $(C_1-C_{12})$ alkylthio,
$R^1$ is Hydrogen or a $(C_1-C_{12})$ alkyl;
$R^2$ is a $(C_1-C_{12})$ alkyl;
d is hydrogen, a halogen, a $(C_1-C_{12})$ alkyl, a $(C_1-C_{12})$ alkoxy, a trifluoromethyl, a nitro group, nitroaryl, nitroalkyl $(C_1-C_{12})$ alkylthio, a phenyl or alkoxyphenyl or aryloxyphenyl and halophenyl,
X is independently an aliphatic, hetrocyclic and hetrocyclic amine.
  a. cyclizing in a reaction vessel, and in an inert atmosphere a compound of Formula I by treatment with a cyclizing agent, to afford a first mass;

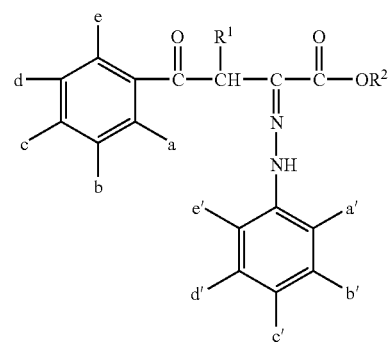

I wherein,
$R^1$ is Hydrogen or a $(C_1-C_{12})$ alkyl;
$R^2$ is a $(C_1-C_{12})$ alkyl;
a, b, c, e, and a' b' c' d' e' are identical or different and are independently hydrogen, a halogen, a $(C_1-C_{12})$ alkyl, a $(C_1-C_{12})$ alkoxy, a trifluoromethyl, a nitro group, nitroaryl, nitroalkyl and $(C_1-C_{12})$ alkylthio.
d is hydrogen, a halogen, a $(C_1-C_{12})$ alkyl, a $(C_1-C_{12})$ alkoxy, a trifluoromethyl, a nitro group, nitroaryl, nitroalkyl $(C_1-C_{12})$ alkylthio, a phenyl or alkoxyphenyl or aryloxyphenyl and halophenyl.
  b. separating excess cyclizing agent;
  c. amidating of the first mass with an amine in an inert atmosphere, and in the presence of a catalyst and optionally with the help of a nucleating agent to afford an amidated mass;
  d. separating the excess of amine from the amidated mass to afford a second mass; and
  e. isolating compound of Formula IV from the second mass.

Typically, the method steps a and b are performed in the same reaction vessel. Preferably, at least two of the method steps a, b and c are performed in the same reaction vessel. Still preferably, at least two of the method steps a, b, c, d and e are performed in the same reaction vessel.

In accordance with a preferred embodiment of the process is carried out in the same reaction vessel.

Typically, the method step of checking for the completion of the amidating reaction is performed before isolating compound of Formula IV from the amidated mass. Typically, the completion of the reaction is checked by at least one technique selected from a group of techniques consisting of GC, TLC, HPTLC, HPLC and NMR.

Preferably, the compound of Formula I is selected from a group of compounds consisting of compounds wherein $R^1$ is Hydrogen, methyl, ethyl, propyl and t-butyl and $R^2$ is a $(C_1-C_6)$ alkyl, a, b, c, e, and a' b' c' d' e' are identical or different and are independently hydrogen, a halogen, a $(C_1-C_6)$ alkyl, and d is hydrogen, a halogen, a $(C_1-C_6)$ alkyl, phenyl.

In accordance with one preferred embodiment of the invention, the compound of Formula I is selected from a group of compounds consisting of compounds wherein, $R^1$ is methyl, ethyl, propyl and $R^2$ is a $(C_1-C_3)$ alkyl;

a, b, c, e, and a' b' c' d' e' are identical or different and are independently hydrogen, chloro, bromo, and d is hydrogen, a halogen.

Typically, the cyclizing agent is selected from a group of compounds consisting of acetic acid, propionic acid, butyric acid, pentanoic acid, isobutyric acid and hexanoic acid. Preferably, the cyclizing agent is acetic acid. Typically, the proportion of the cyclizing agent to the compound of Formula I is in the range of about 1:5 to about 1:50. Preferably, the proportion of the cyclizing agent to the compound of Formula I is in the range of about 1:8 to about 1:20.

Typically, the method steps a is carried out at a temperature ranging from about 30° C. to about the boiling point of the cyclizing agent. Typically, the cyclizing is carried out for about 2 to about 36 hours. Typically, the method step of separating excess cyclizing agent includes the method step of separating the cyclizing agent from the first mass by distillation. Preferably, the step of separating the excess cyclizing agent includes an additional step of treating the first mass with a scavenging agent and further removing traces of the cyclizing agent and scavenging agent by co-distillation. Typically, the separated cyclizing agent is reused. Typically, the scavenging agent is at least one scavenging agent selected from a group of compounds consisting of aromatic solvents, halogenated solvents, ethers and alcohols. Preferably, the scavenging agent is an aromatic solvent. Still preferably, scavenging agent is at least one agent selected from a group of compounds consisting of toluene and xylene. Alternatively, the scavenging agent is a halogenated solvent. Still alternatively, the scavenging agent is at least one agent selected from a group of compounds consisting of MDC, carbon tetrachloride, chloroform and EDC. Still alternatively, the scavenging agent is an ether and an alcohol. Still alternatively, the scavenging agent is at least one agent selected from a group of compounds consisting of ethyl ether, di-isopropyl ether, MTBE, isopropanol, butanol and isobutanol.

Typically, the amine is selected from a group of amines consisting of:
N-aminopiperidine,
N-methyl-N-aminopiperidine,
N-ethyl-N-aminopiperdine,
N-propyl-N-aminopiperidine,
N-isopropyl-N-aminopiperidine,
N-butyl-N-aminopiperdine,
N-isobutyl-N-aminopiperidine,
N-t-butyl-N-aminopiperidine,
N-pentyl-N-aminopiperdine,
3-methylcyclohexylamine,
2,6-dimethylcyclohexylamine,
2-methoxycyclohexylamine,
4-ethylcyclohexylamine,
N-ethyl-1-adamantylamine, and
2-azabicyclo[2.2.2]octan-2-yl-amine,
Preferably, the amine is selected from a group of amines consisting of:
N-aminopiperidine,
N-methyl-N-aminopiperidine,
N-ethyl-N-aminopiperdine,
N-propyl-N-aminopiperidine,
N-isopropyl-N-aminopiperidine,
N-butyl-N-aminopiperdine and
N-isobutyl-N-aminopiperidine.

In accordance with one preferred embodiment of the invention, the amine that is used, is N-aminopiperidine. Typically, the quantity of amine used in method step c with respect to the quantity of compound of Formula I is in the range of about 1:1 to about 1:20. Typically, the method steps of amidating is carried out at a temperature ranging from about 30° C. to the boiling point of the amine. Typically, the step of amidating is carried out for about 6 hours to 24 hours. Typically, the catalyst is a metal salt. Preferably, the catalyst is at least one metal salt of a metal selected from a group of metals consisting of manganese, calcium, zinc, cobalt, antimony, titanium and tin. Still preferably, the catalyst is at least one compound selected from a group of compounds consisting of manganese acetate, titanium acetate, calcium acetate, zinc acetate, antimony trioxide, antimony triacetate, cobalt acetate, tin oxide, alkyl-titanate and alkoxytitanate.

In accordance with one preferred embodiment of the invention, the catalyst is manganese acetate dihydrate. Typically, the proportion of catalyst with respect to the compound of Formula I is in the range of 30 ppm to about 100,000 ppm. Preferably, the proportion of catalyst with respect to the compound of Formula I is in the range of 100 ppm to about 50,000 ppm. Typically, the nucleating agent is at least one agent selected from a group of nucleating agents consisting of sodium acetate, sorbitol, sodium benzoate, sodium salicylate, nyacol, sodium sorbitrate, nano silica, tungsten trioxide, 3,5-di-t-butyl-4-hydroxyphenyl propionic acid methyl ester, and ethylene acrylic acid sodium ionomer. Typically, the method step of separating excess amine includes the method step of separating the amine from the amidated mass by distillation. Preferably, the step of separating the excess amine includes an additional step of treating the amidated mass with a scavenging agent and further removing the traces of the amine and the scavenging agent by co-distillation. Typically, the scavenging agent is at least one scavenging agent selected from a group of compounds consisting of aromatic solvents, halogenated solvents, ethers and alcohols.

Typically, the separated amine is reused.

Typically, the method step of isolating compound of Formula IV from the second mass comprises:
treating the second mass with a water insoluble solvent and an aqueous alkali to form a first biphasic mixture with suspended insoluble particles;
filtering the biphasic mixture to remove the insoluble particles to obtain a clear biphasic mixture;
separating the compound of Formula IV in crude form, from the clear biphasic mixture; and purifying the compound of Formula IV as a base or as an acid addition salt from the separated crude form of compound of Formula IV in crude form.

Typically, the water insoluble solvent is selected from a group of solvents consisting of ethyl acetate, propyl acetate, isopropyl acetate, butyl acetate, methyl ethyl ketone, methylisobutyl ketone, ethyl ether, diisopropyl ether, methyl t-butylether, MDC, EDC and chloroform. Typically, the aqueous alkali solution is at least one aqueous alkali selected from a group of alkalies consisting of sodium carbonate, sodium bicarbonate, potassium carbonate, potassium bicarbonate, sodium hydroxide and potassium hydroxide. Typically, the proportion of the water insoluble solvent with respect to the quantity of compound of Formula I is in the range of about 1:5 to about 1:50. Preferably, the proportion of the aqueous alkali with respect to the quantity of the compound of Formula I is in the range of about 5 to about 20. Typically, the method step of separating the compound of Formula IV in crude form from the clear biphasic mixture comprises:

separating the aqueous phase from the first biphasic mixture and retaining a first organic phase containing the compound of Formula IV in solution form;

treating the first organic phase with an aqueous solution of a sequestering agent resulting in a second biphasic mixture in the reaction vessel, separating the aqueous phase from the second biphasic mixture and retaining a second organic phase containing the compound of Formula IV in solution form;

treating the second organic phase with saturated aqueous solution of sodium chloride to from a third biphasic mixture, separating the aqueous phase from the third biphasic mixture and retaining a third organic phase containing the compound of Formula IV in solution form;

removing the solvent from the third organic phase and retaining the crude compound of Formula IV.

Typically, the method step of purifying the compound of Formula IV as a base or as an acid addition salt from the separated compound of Formula IV in crude form includes the method step of purifying the retained crude compound of Formula IV in the reaction vessel by treating it with water insoluble aliphatic solvent followed by isolation of the compound of Formula IV as a base by filtration. Typically, the aliphatic solvent is at least one solvent selected from a group of aliphatic solvents consisting of hexane, heptane and octane.

Alternatively, the method step of purifying the compound of Formula IV as as an acid addition salt from the separated compound of Formula IV in crude form includes following steps:

adding a protic solvent like methanol, ethanol, isopropanol, acetone, methylisobutylketone to the compound of Formula IV in crude from;

stirring the reaction mass to obtain a clear solution followed by addition of an acid; and stirring and cooling the resulting slurry followed by filtration thereof to afford an acid addition salt of compound of Formula IV.

Typically, the acid is selected from a group of acids consisting of sulphuric acid, hydrochloric acid, hydrobromic acid, hydrofluoric acid, phosphoric acid and nitric acid, citric acid, oxalic acid, fumeric acid, maleic acid, tannic acid, tartaric acid, benzenesulfonic acid, methanesulfonic acid, para-toluenesulfonic acid, pamoic acid, stearic acid, napthanoic acid.

Still alternatively, the method step of purifying the compound of Formula IV from the separated compound of Formula IV comprises:

adding a protic solvent like methanol, ethanol, isopropanol, acetone, methylisobutylketone to the compound of Formula IV in crude from;

stirring the reaction mass to obtain a clear solution followed by addition of 8chloro-theophylline, and stirring and cooling the resulting slurry followed by filtration thereof to afford a theoclate salt of compound of Formula IV.

DETAILED DESCRIPTION

Processes known in the art for preparation of Pyrazole-3-carboxamide derivatives involve multi-step, multi-reactor lengthy synthetic routes. It is because of this reason, these processes are uneconomical and complex. Furthermore, these processes also employ toxic reagents such as chlorinating agents including thionyl chloride, phosphorous trichloride, phosphorous oxychloride and the like.

The present invention discloses a hitherto unreported route for preparation of Pyrazole-3-carboxamide derivatives.

One of the several distinctive features of this process is that it can be adapted for a "One Pot Reaction" as a commercially adoptable, viable and economical strategy for synthesis of Pyrazole-3-carboxamide derivatives. Furthermore, the said "one pot Reaction" strategy avoids a lengthy separation and purification process, saves time and resources while increasing chemical yield.

Scheme III describes the process in accordance with the present invention.

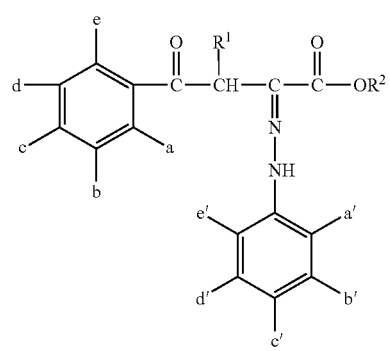

Scheme III

Cyclizing agent
Toluene/xylene: Scavenging agents
Amine + Catalyst + Nucleating agent.

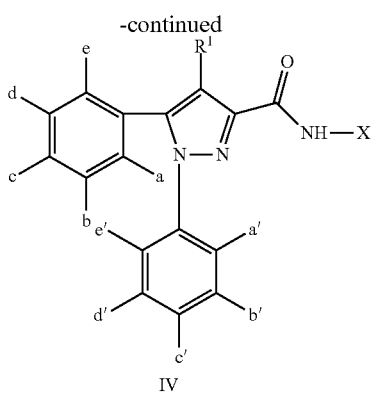

IV

Wherein, a, b, c, e, and a' b' c' d' e' are identical or different and are independently hydrogen, a halogen, a ($C_1$-$C_{12}$) alkyl, a ($C_1$-$C_{12}$) alkoxy, a trifluoromethyl, a nitro group, nitroaryl, nitroalkyl and ($C_1$-$C_{12}$) alkylthio.

$R^1$ is Hydrogen or a ($C_1$-$C_{12}$) alkyl;
$R^2$ is a ($C_1$-$C_{12}$) alkyl;
d is hydrogen, a halogen, a ($C_1$-$C_{12}$) alkyl, a ($C_1$-$C_{12}$) alkoxy, a trifluoromethyl, a nitro group, nitroaryl, nitroalkyl ($C_1$-$C_{12}$) alkylthio, a phenyl or alkoxyphenyl or aryloxyphenyl and halophenyl,
X is independently an aliphatic, hetrocyclic and hetrocyclic amine.

Described herein below is the process in accordance with this invention.

Step a: Cyclization

Cyclizing in a reaction vessel, and in an inert atmosphere a compound of Formula I by treatment with a cyclizing agent, to afford a first mass:

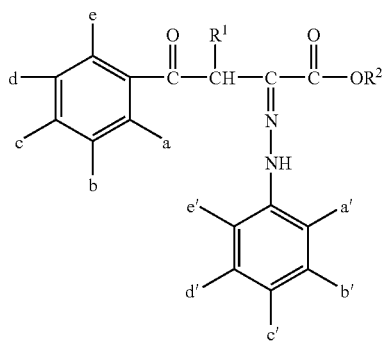

I wherein, $R^1$ is Hydrogen or a ($C_1$-$C_{12}$) alkyl; and $R^2$ is a ($C_1$-$C_{12}$) alkyl;
a, b, c, e, and a' b' c' d' e' are identical or different and are independently hydrogen, a halogen, a ($C_1$-$C_{12}$) alkyl, a ($C_1$-$C_{12}$) alkoxy, a trifluoromethyl, a nitro group, nitroaryl, nitroalkyl and ($C_1$-$C_{12}$) alkylthio
d is hydrogen, a halogen, a ($C_1$-$C_{12}$) alkyl, a ($C_1$-$C_{12}$) alkoxy, a trifluoromethyl, a nitro group, nitroaryl nitroalkyl ($C_1$-$C_{12}$) alkylthio, a phenyl or alkoxyphenyl or aryloxyphenyl and halophenyl.

Typically, the compound of Formula I is selected from a group of compounds consisting of compounds wherein $R^1$ is Hydrogen, methyl ethyl, propyl and t-butyl and $R^2$ is a ($C_1$-$C_6$) alkyl,
a, b, c, e, and a' b' c' d' e' are identical or different and are independently hydrogen, a halogen, a ($C_1$-$C_6$) alkyl, and d is hydrogen, a halogen, a ($C_1$-$C_6$) alkyl, phenyl.

Preferably, compound of Formula I is selected from a group of compounds consisting of compounds wherein, $R^1$ is methyl ethyl, propyl and $R^2$ is a ($C_1$-$C_3$) alkyl;
a, b, c, e, and a' b' c' d' e' are identical or different and are independently hydrogen, chloro, bromo, and
d is hydrogen, a halogen.

Typically, the cyclizing agent is selected from a group of compounds consisting of acetic acid, propionic acid, butyric acid, pentanoic acid, isobutyric acid and hexanoic acid. Preferably, acetic acid is used as the cyclizing agent. Typically, the proportion of the cyclizing agent to the compound of Formula I is in the range of about 1:5 to about 1:50. Preferably, the proportion of the cyclizing agent to the compound of Formula I is in the range of about 1:8 to about 1:20. Cyclization is typically carried out at a temperature ranging from about 30° C. to about the boiling point of the cyclizing agent for time period of a about 2 to 36 hours.

Step b: Removal of Cyclizing Agent

Separating Excess Cyclizing Agent:

This method step includes the method step of separating the cyclizing agent from the first mass by distillation. Furthermore, the first mass is then treated with a scavenging agent for removing traces of the cyclizing agent. Typically, the scavenging agent is then removed by co-distillation.

Typically, the separated cyclizing agent is reused. Typically, the scavenging agent is at least one scavenging agent selected from a group of compounds consisting of aromatic solvents, halogenated solvents, ethers and alcohols.

Preferably, the scavenging agent is at least one agent selected from a group of compounds consisting of toluene and xylene. Alternatively, the scavenging agent is at least one agent selected from a group of compounds consisting of MDC, carbon tetrachloride, chloroform and EDC. Still alternatively, the scavenging agent is at least one agent selected from a group of compounds consisting of ethyl ether, di-isopropyl ether, MTBE, isopropanol, butanol and isobutanol.

Step c: Amidation

Amidating of the first mass with an amine in an inert atmosphere, and in the presence of a catalyst and optionally with the help of a nucleating agent to afford an amidated mass:

Typically, amine is selected from a group of amines consisting of:
N-aminopiperidine,
N-methyl-N-aminopiperidine,
N-ethyl-N-aminopiperdine,
N-propyl-N-aminopiperidine,
N-isopropyl-N-aminopiperidine,
N-butyl-N-aminopiperdine,
N-isobutyl-N-aminopiperidine
N-t-butyl-N-aminopiperidine,
N-pentyl-N-aminopiperdine,
3-methylcyclohexylamine,
2,6-dimethylcyclohexylamine,
2-methoxycyclohexylamine,
4-ethylcyclohexylamine,
N-ethyl-1-adamantylamine, and
2-azabicyclo[2.2.2]octan-2-yl-amine, Preferably, the amine is selected from a group of amines consisting of:
N-aminopiperidine,
N-methyl-N-aminopiperidine,
N-ethyl-N-aminopiperdine,
N-propyl-N-aminopiperidine,
N-isopropyl-N-aminopiperidine,
N-butyl-N-aminopiperdine and
N-isobutyl-N-aminopiperidine.

In accordance with one preferred embodiment of this invention, the amine used is N-aminopiperidine.

Typically, the quantity of amine used in method step of amidating, with respect to the quantity of compound of Formula I is in the range of about 1:1 to about 1:20.

Typically, the catalyst is a metal salt. Preferably, the catalyst is at least one metal salt of a metal selected from a group of metals consisting of manganese, calcium, zinc, cobalt, antimony, titanium and tin. Still preferably the catalyst is at least one compound selected from a group of compounds consisting of manganese acetate, titanium acetate, calcium acetate, zinc acetate, antimony trioxide, antimony triacetate, cobalt acetate, tin oxide, alkyl-titanate and alkoxytitanate. In accordance with one preferred embodiment of the invention, manganese acetate dihydrate is used as a catalyst. Typically, the proportion of catalyst with respect to the compound of Formula I is in the range of 30 ppm to about 100,000 ppm. Preferably, the proportion of catalyst with respect to the compound of Formula I is in the range of 100 ppm to about 50,000 ppm.

Typically, the nucleating agent is at least one agent selected from a group of nucleating agents consisting of sodium acetate, sorbitol, sodium benzoate, sodium salicylate, nyacol, sodium sorbitrate, nano silica, tungsten trioxide, 3,5-di-t-butyl-4-hydroxyphenyl propionic acid methyl ester, and ethylene acrylic acid sodium ionomer is optionally used with the catalyst.

Typically, the method step of amidating is carried out at a temperature ranging from about 30° C. to the boiling point of the amine. Typically, the step of amidating is carried out for about 6 hours to 24 hours. Typically, the completion of the amidating reaction is checked by at least one technique selected from a group of techniques consisting of GC, TLC, HPTLC, HPLC and NMR.

Step d: Separation of Excess of Amine

Typically, the excess of amine from the amidated mass is separated to afford a second mass by distillation.

Preferably, the method step of separating excess of amine includes the method step of separating the amine from the amidated mass by distillation. Preferably, the step of separating the excess amine includes an additional method step of treating the amidated mass with a scavenging agent and further removing the traces of the amine and the scavenging agent by co-distillation. Typically, the scavenging agent is at least one scavenging agent selected from a group of compounds consisting of aromatic solvents, halogenated solvents, ethers and alcohols. The excess of amine, separated by distillation is reused thereby improving the economy of the overall process.

Step e: Isolation of Compound of Formula IV.

The compound of Formula IV is then isolated from the amidated mass.

Typically, the method step of isolating compound of Formula IV from the second mass comprises:
treating the second mass with a water insoluble solvent and an aqueous alkali solution to form a first biphasic mixture with suspended insoluble particles;
filtering the biphasic mixture to remove the insoluble particles to obtain a clear biphasic mixture;
separating the compound of Formula IV in crude form from the clear biphasic mixture; and
purifying the compound of Formula IV as a base or as an acid addition salt from the separated compound of Formula IV in crude form.

Typically, the water insoluble solvent is selected from a group of solvents consisting of ethyl acetate, propyl acetate, isopropyl acetate, butyl acetate, methyl ethyl ketone, methylisobutyl ketone, ethyl ether, diisopropyl ether, methyl t-butylether, MDC, EDC and chloroform. Typically, the aqueous alkali solution is at least one aqueous alkali selected from a group of alkalies consisting of sodium carbonate, sodium bicarbonate, potassium carbonate, potassium bicarbonate, sodium hydroxide and potassium hydroxide.

Typically, the proportion of the water insoluble solvent with respect to the quantity of compound of Formula I is in the range of about 1:5 to about 1:50. Typically, the proportion of the aqueous alkali with respect to the quantity of the compound of Formula I is in the range of about 5 to about 20.

Typically, the method of separation of compound of Formula IV in crude form, from the biphasic mixture comprises:
separating the aqueous phase from the first biphasic mixture and retaining a first organic phase containing the compound of Formula IV in solution form;
treating the first organic phase with an aqueous solution of a sequestering agent resulting in a second biphasic mixture in the reaction vessel, separating the aqueous phase from the second biphasic mixture and retaining a second organic phase containing the compound of Formula IV in solution form;
treating the second organic phase with saturated aqueous solution of, sodium chloride to from a third biphasic mixture,
separating the aqueous phase from the third biphasic mixture and retaining a third organic phase containing the compound of Formula IV in solution form;
removing the solvent from the third organic phase and retaining the crude form of compound of Formula IV.

Typically, the method step of purifying the compound of Formula IV as a base from the separated compound of Formula IV includes the method step of purifying the retained crude compound of Formula IV in the reaction vessel by treating it with water insoluble aliphatic solvent followed by isolation of the compound of Formula IV as a base by filtration. Typically, the aliphatic solvent is at least one solvent selected from a group of aliphatic solvents consisting of hexane, heptane and octane.

Alternatively, the method step of purifying the compound of Formula IV as an acid addition salt from the separated compound of Formula IV comprises:
adding a protic solvent like methanol, ethanol, isopropanol, acetone, methylisobutylketone to the compound of Formula IV in crude from;
stirring the reaction mass to obtain a clear solution followed by addition of an acid; and
stirring and cooling the resulting slurry followed by filtration thereof to afford an acid addition salt of compound of Formula IV.

Typically, the acid is selected from a group of acids consisting of sulphuric acid, hydrochloric acid, hydrobromic acid, hydrofluoric acid, phosphoric acid and nitric acid, citric acid, oxalic acid, fumeric acid, maleic acid, tannic acid, tartaric acid, benzenesulfonic acid, methanesulfonic acid, para-toluenesulfonic acid, pamoic acid, stearic acid, napthanoic acid.

Still alternatively, the method step of purifying the compound of Formula IV from the separated compound of Formula IV comprises:
adding a protic solvent like methanol, ethanol, isopropanol, acetone, methylisobutylketone to the compound of Formula IV in crude from;
stirring the reaction mass to obtain a clear solution followed by addition of 8chloro-theophylline; and stirring and cooling the resulting slurry followed by filtration thereof to afford a theoclate salt of compound of Formula IV.

Most advantageously, all the method steps, from cyclization till isolation of Compound of Formula IV are carried out in the same reaction vessel. However one can perform the method steps of cyclization and removal of excess of cyclizing agent in the same reaction vessel.

Alternatively, at least two of the method steps from the group of method steps consisting of cyclization, removing of excess of cyclizing agent and amidating of the first mass are carried out in the same reaction vessel. Still alternatively, at least two of the method steps from the group of method steps consisting of cyclization, removing excess of cyclizing agent, amidating, removing excess of amine and isolating compound of Formula IV are performed in the same reaction vessel.

EXAMPLES

The invention will now be described with the help of following non-limiting examples.

Example 1

5-(4-Chlorphenyl)-1-(2,4-dichlorophenyl)-4-methyl-N-piperidin-1-yl)-1H-pyrazole-3-carboxamide 10.0 gms of ethyl-3-(4-chlorobenzoyl)-2-[(2,4-dichlorophenyl)-hydrazono]-butyrate (Prepared by reacting 2-oxo-3-(4-chlorobenzoyl)-ethylbutyrate and 2,4-dichlorophenyl hydrazine HCl.) was reacted with 60 ml acetic acid under reflux, in Nitrogen atmosphere for 16 hours. The acetic acid was then distilled under reduced pressure for recovery and reuse. The residue was added with 40 ml toluene and was distilled under reduced pressure to obtain uniform mass. To the mass, was added 15 ml N-aminopiperdine in Nitrogen atmosphere, 0.5 gm of manganese acetate dihydrate and the reaction mass was heated to 140° C. to 145° C. for 20 hours. The reaction progress was monitored on TLC. At the end of the 20 hour period, the excess amine was distilled under reduced pressure. 8 ml of N-aminopiperidine was recovered. The reaction mass was then added with 80 ml water and 100 ml of ethyl acetate and stirred for 15 minutes. The biphasic mixture was further added with 10 ml of 5% sodium bicarbonate aqueous solution and the mass was stirred for 10 minutes. The entire biphasic mass was filtered through a filter-aid bed to remove metallic salts. The phases were then separated. The aqueous phase was extracted with 2×25 ml ethyl acetate. The combined ethyl acetate phase was washed with 25 ml of 1% aqueous Sodium EDTA Solution followed by 2×25 ml saturated NaCl solution. The organic phase was then dried with anhydrous $Na_2SO_4$ and then the solvent was recovered under reduced pressure. The residue was further added with 25 ml hexane and then it was distilled. 40 ml of hexane was then added and stirred for 2 hours to obtain product slurry. The solid was then filtered and dried under vacuum to obtain off-white product with a Melting Point of 146-52° C., dry mass 6.3 gm. The structure was confirmed by IR and NMR Spectra.

NMR (DMSO-d6 1H it 200 MHz): 1.32 ppm 2H; 1.56 ppm 4H; 2.24 ppm: s: 3H; 4.1 ppm: d: 2H; 7.32 ppm: d: 2H; 7.39 ppm: d: 2H; 7.64 ppm: dd: 1H; 7.79 ppm: d: 1H; 7.81 pprn: dl: H; 9.08 ppm: s: 1H.

IR Spectra:
$\lambda cm^{-1}$ 3647, 3522, 3381, 3319, 2947, 2706, 2671, 1699, 1541, 1496, 1483, 1055, 922, 901, 687, 662, 554, 521, 486.

Example 2

Preparation of hydrochloride salt of 5-(4-Chlorphenyl)-1-(2,4-dichlorophenyl)-4-methyl-N-piperidin-1-yl)-1H-pyrazole-3-carboxamide The process as described in example 1 up to the method step of addition of 25 ml of hexane up to its distillation was repeated.

The residue was further added with 50 ml acetone and stirred for 20 minutes. 0.2 gm of activated charcoal was then added, stirred for 30 minutes, and filtered through filter aid. The filter bed was washed with 10 ml acetone and combined with main filtrate. The clear solution was added under Nitrogen with dilute HCl solution(6 ml conc. HCl +5 ml deionised water) within a period of 5 minutes under stirring. The mass was stirred at room temperature for 6 hours, then chilled to 10° C. and then stirred for additional 4 hours. The crystalline slurry was filtered, washed with chilled acetone and the product was dried under vacuum at 60° C. to 70° C. Output: Dry weight 6.0 gm. white solid, melting point: 223 to 238° C.

Example 3

5-(4-Chlorphenyl)-1-(2,4-dichlorophenyl)-4-methyl-N-piperidin-1-yl)-1H-pyrazole-3-carboxamide.

10.0 gms of ethyl-3-(4-chlorobenzoyl)-2-[(2,4-dichlorophenyl)-hydrazono]-butyrate (Prepared by reacting 2-oxo-3-(4-chlorobenzoyl)-ethylbutyrate and 2,4-dichlorophenyl hydrazine HCl) is reacted with 70 ml propionic acid under reflux, under Nitrogen atmosphere for 16 hours. The propionic acid is then distilled under reduced pressure for recovery and reuse. The residue was added with 50 ml toluene and was distilled under reduced pressure to obtain uniform mass. To the mass, was added 15 ml N-aminopiperdine in Nitrogen atmosphere, 0.3 gm of manganese acetate dihydrate and the reaction mass was heated to 140° C. to 145° C. for 20 hours. The reaction progress was monitored on TLC. At the end of the 20 hour period, the excess amine was distilled under reduced pressure. 8 ml of N-aminopiperidine was recovered. The reaction mass was then added with 80 ml water and 100 ml of ethyl acetate and stirred for 15 minutes. The biphasic mixture was further added with 10 ml of 5% sodium bicarbonate aqueous solution and the mass was stirred for 10 minutes. The entire biphasic mass was filtered through a filter-aid bed to remove metallic salts. The phases were then separated. The aqueous phase was extracted with 2×25 ml ethyl acetate. The combined ethyl acetate phase was washed with 25 ml of 1% aqueous Sodium EDTA Solution followed by 2×25 ml saturated. NaCl solution. The organic phase was then dried with anhydrous $Na_2SO_4$ and then the solvent was recovered under reduced pressure. The residue was further added with 25 ml hexane and then it was distilled. 40 ml of hexane was then added and stirred for 2 hours to obtain product slurry. The solid was then filtered and dried under vacuum to obtain off-white product with a Melting Point of 146-52° C., dry mass 4.5 gm. The structure was confirmed by IR and NMR Sprectra.

Example 4

5-(4-Chlorphenyl)-1-(2,4-dichlorophenyl)-4-methyl-N-piperidin-1-yl)-1H-pyrazole-3-carboxamide 15.0 gms of ethyl-3-(4-chlorobenzoyl)-2-[(2,4-dichlorophenyl)-hydrazono]-butyrate (Prepared by reacting 2-oxo- 3-(4-chlorobenzoyl)-ethylbutyrate and 2,4-dichlorophenyl hydrazine HCl) is reacted with 105 ml propionic acid under reflux, in Nitrogen atmosphere for 16 hours. The propionic acid was then distilled under reduced pressure for recovery and reuse. The residue was added with 80 ml xylene and was distilled under reduced pressure to obtain uniform mass. To the mass, was added 25 ml N-aminopiperdine in Nitrogen atmosphere, 0.6 gm of manganese acetate dihydrate, followed by 0.1 gm sodium acetate as a nucleating agent and the reaction mass was heated to 140° C. to 145° C. for 20 hours. The reaction progress was monitored on TLC. At the end of the 20 hour period, the excess amine was distilled under reduced pressure. 14 ml of N-aminopiperidine was recovered. The reaction mass was then added with 80 ml water and 150 ml of butyl acetate and stirred for 15 minutes. The biphasic mixture was further added with 15 ml of 5% sodium carbonate aqueous solution and the mass was stirred for 10 minutes. The entire biphasic mass was filtered through a filter-aid bed to remove metallic salts. The phases were then separated. The aqueous phase was extracted with 2×50 ml butyl acetate. The combined butyl acetate phase was washed with 40 ml of 1% aqueous Sodium EDTA Solution followed by 2×50 ml saturated NaCl solution. The organic phase was then dried with anhydrous $Na_2SO_4$ and then the solvent was recovered under reduced pressure. The residue was further added with 50 ml heptane and then it was distilled. 100 ml of heptane was then added and stirred for 2 hours to obtain product slurry. The solid was then filtered and dried under vacuum to obtain off-white product with a Melting Point of 146-52° C., dry mass 7.1 gm. The structure was confirmed by IR and NMR Spectra.

Example 5

The process as described in example 4 was repeated up to the method step of addition of 50 ml of heptane followed by its distillation. 70 ml of isopropanol was added to the reaction mixture and was stirred to obtain a clear solution. Subsequently, the clear solution was added in Nitrogen with dilute HCl solution (8 ml conc. HCl +9 ml deionised water) within a period of 5 minutes under stirring. The mass was stirred at room temperature for 6 hours, then chilled to 10° C. and then stirred for additional 4 hours. The crystalline slurry was filtered, washed with chilled isopropanol and the product was dried under vacuum at 60° C. to 70° C. Output: Dry weight 7.5 gm. A white crystalline solid with a melting point in the range of 224 to 237° C. was obtained.

Example 6

N-piperidino-5-(4-bromophenyl)-1-(2,4-dichlorophenyl)-4-ethyl Pyrazole-3-carboxamide 10.0 gm ethyl-3-(4-bromobenzoyl)-2-[2,4-dichlorophenyl)-hydrazono]-pentanoate (prepared by reacting 3-(4-bromobenzoyl)-2-oxo-ethyl pentanoate with 2,4 dichlorophenylhydrazine hydrochloride)was reacted with 60 ml of acetic acid under reflux in Nitrogen atmosphere for 16 hours. The acetic acid was then distilled under reduced pressure for reuse. The residue was added with 50 ml toluene and it was distilled under vacuum. The mass was then added with 18 ml N-Aminopiperidine and 0.5 gm of Manganese acetate dihydrate and heated to 140° C. to 145° C. and maintained at that temperature for 24 hours in Nitrogen atmosphere. The progress of the reaction was monitored by TLC. At the end of 24 hours, the excess amine was recovered by distilling it under reduced pressure. The residue was then added with 100 ml ethyl acetate, 80 ml water and 10 ml 5% sodium bicarbonate solution. It was stirred for 20 minutes. The biphasic mixture was then filtered through a bed of filter aid to remove inorganic salts. The phases were then separated, the washed aqueous phase was combined with main ethyl acetate phase. The organic phase was then washed with 25 ml of 1% EDTA Solution in water and then with 2×25 ml of aqueous saturated NaCl solution. The ethyl acetate layer was then subjected to distillation under vacuum. The residue was added with 50 ml of hexane. It was then distilled. The same operation was repeated twice. The residue was then added with 80 ml hexane and stirred for 6 hours at 10° C. It was then filtered, washed with chilled hexane and dried under vacuum. Creamish solid, 5.2 gm, with a MP of about 112-115° C. was obtained.

NMR: 1.03 ppm: t: 3H; 1.23-1.63 ppm: m: 6H; 2.62 ppm: q: 2H; 2.82 ppm: m: 4H; 7.10 ppm: d: 2H; 7.48-7.83 ppm: m: 5H; 9.06 ppm: s: 1H.

While considerable emphasis has been placed herein on the specific steps of the preferred process, it will be appreciated that many steps can be made and that many changes can be made in the preferred steps without departing from the principles of the invention. These and other changes in the preferred steps of the invention will be apparent to those skilled in the art from the disclosure herein, whereby it is to be distinctly understood that the foregoing descriptive matter is to be interpreted merely as illustrative of the invention and not as a limitation.

The invention claimed is:

1. A process for preparation of compounds of Formula IV:

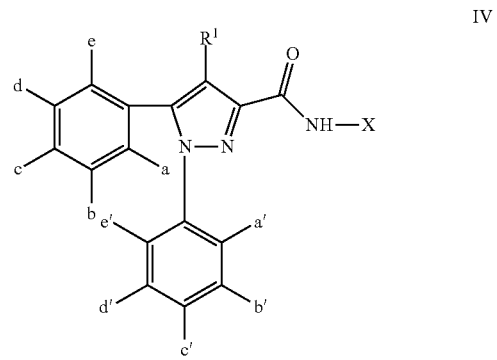

wherein, a, b, c, e, a', b', c', d', and e' are identical or different and are independently hydrogen, a halogen, a $(C_1-C_{12})$ alkyl, a $(C_1-C_{12})$ alkoxy, a trifluoromethyl, a nitro group, nitroaryl, nitroalkyl or $(C_1-C_{12})$ alkylthio $R^1$ is Hydrogen or a $(C_1-C_{12})$ alkyl;

d is hydrogen, a halogen, a $(C_1-C_{12})$ alkyl, a $(C_1-C_{12})$ alkoxy, a trifluoromethyl, a nitro group, nitroaryl, nitroalkyl $(C_1-C_{12})$ alkylthio, a phenyl or alkoxyphenyl or aryloxyphenyl, or halophenyl; and X is independently an aliphatic, or heterocyclic amine, said method comprising the steps of:

a. cyclizing in a reaction vessel, and in an inert atmosphere a compound of Formula I by treatment with a cyclizing agent, to afford a first mass;

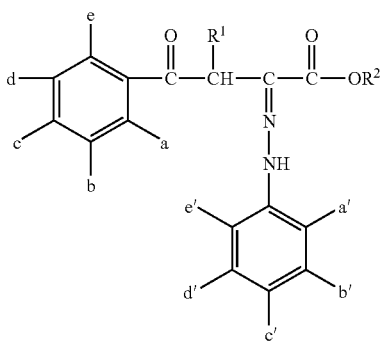

wherein,
R¹ is Hydrogen or a ($C_1$-$C_{12}$) alkyl;
R² is a ($C_1$-$C_{12}$) alkyl;
  a, b, c, e, a', b', c', d', and e' are identical or different and are independently hydrogen, a halogen, a ($C_1$-$C_{12}$) alkyl, a ($C_1$-$C_{12}$) alkoxy, a trifluoromethyl, a nitro group, nitroaryl, nitroalkyl or ($C_1$-$C_{12}$) alkylthio,
  d is hydrogen, a halogen, a ($C_1$-$C_{12}$) alkyl, a ($C_1$-$C_{12}$) alkoxy, a trifluoromethyl, a nitro group, nitroaryl, nitroalkyl ($C_1$-$C_{12}$ alkylthio, a phenyl or alkoxyphenyl or aryloxyphenyl or halophenyl;
b. separating excess cyclizing agent;
c. amidating of the first mass with an amine in an inert atmosphere, and in the presence of a catalyst and optionally with the help of a nucleating agent to afford an amidated mass;
d. separating the excess of amine from the amidated mass to afford a second mass;
e. isolating compound of Formula IV from the second mass.

2. A process as claimed in claim 1, wherein the method steps a and b are performed in the same reaction vessel.

3. A process as claimed in claim 1, wherein at least two of the method steps a, b and c are performed in the same reaction vessel.

4. A process as claimed in claim 1, wherein at least two of the method steps a, b, c, d and e are performed in the same reaction vessel.

5. A process as claimed in claim 1, wherein the process is carried out in the same reaction vessel.

6. A process as claimed in claim 1, which includes the method step of checking for the completion of the amidating reaction before isolating compound of Formula IV from the amidated mass.

7. A process as claimed in claim 6, wherein the completion of the reaction is checked by at least one technique selected from a group of techniques consisting of GC, TLC, HPTLC, HPLC and NMR.

8. A process as claimed in claim 1, wherein the compound of Formula I is selected from a group of compounds consisting of compounds wherein R¹ is Hydrogen, methyl, ethyl, propyl or t-butyl and
  R² is a ($C_1$-$C_6$) alkyl;
  a, b, c, e, a', b', c', d', and e' are identical or different and are independently hydrogen, a halogen, a ($C_1$-$C_6$) alkyl; and
  d is hydrogen, a halogen, a ($C_1$-$C_6$) alkyl, or phenyl.

9. A process as claimed in claim 1, wherein the compound of Formula I is selected from a group of compounds consisting of compounds wherein, R¹ is methyl, ethyl, or propyl;
  R² is a ($C_1$-$C_3$) alkyl;
  a, b, c, e, a', b', c', d', and e' are identical or different and are independently hydrogen, chloro, or bromo; and
  d is hydrogen or a halogen.

10. A process as claimed in claim 1, wherein the cyclizing agent is selected from the group consisting of acetic acid, propionic acid, butyric acid, pentanoic acid, isobutyric acid and hexanoic acid.

11. A process as claimed in claim 10, wherein the cyclizing agent is acetic acid.

12. A process as claimed in claim 1, wherein the proportion of the cyclizing agent to the compound of Formula I is in the range of about 1:5 to about 1:50.

13. A process as claimed in claim 12, wherein the proportion of the cyclizing agent to the compound of Formula I is in the range of about 1:8 to about 1:20.

14. A process as claimed in claim 1, wherein the method step a is carried out at a temperature ranging from about 30° C. to about the boiling point of the cyclizing agent.

15. A process as claimed in claim 1, wherein the cyclizing is carried out for about 2 to 36 hours.

16. A process as claimed in claim 1, wherein the method step of separating excess cyclizing agent includes the method step of separating the cyclizing agent from the first mass by distillation.

17. A process as claimed in claim 16, wherein the separated cyclizing agent is reused.

18. A process as claimed in claim 1, wherein the step of separating the excess cyclizing agent includes an additional step of treating the first mass with a scavenging agent and further removing traces of the cyclizing agent and scavenging agent by co-distillation.

19. A process as claimed in claim 18, wherein the scavenging agent is at least one scavenging agent selected from the group consisting of aromatic solvents, halogenated solvents, ethers and alcohols.

20. A process as claimed in claim 19, wherein the scavenging agent is an aromatic solvent.

21. A process as claimed in claim 20, wherein the scavenging agent is at least one agent selected from the group consisting of toluene and xylene.

22. A process as claimed in claim 1, wherein the scavenging agent is a halogenated solvent.

23. A process as claimed in claim 22, wherein, the scavenging agent is at least one agent selected from the group consisting of MDC, carbon tetrachloride, chloroform and EDC.

24. A process as claimed in claim 1, wherein the scavenging agent is an ether and an alcohol.

25. A process as claimed in claim 24, wherein the scavenging agent is at least one agent selected from the group consisting of ethyl ether, di-isopropyl ether, MTBE, isopropanol, butanol and isobutanol.

26. A process as claimed in claim 1, wherein the amine is selected from the group consisting of:
  N-aminopiperidine,
  N-methyl-N-aminopiperidine,
  N-ethyl-N-aminopiperdine,
  N-propyl-N-aminopiperidine,
  N-isopropyl-N-aminopiperidine,
  N-butyl-N-amniopiperdine,
  N-isobutyl-N-aminopiperidine
  N-t-butyl-N-aminopiperidine,
  N-pentyl-N-aminopiperdine,
  3-methylcyclohexylamine,
  2,6-dimethylcyclohexylamine,
  2-methoxycyclohexylamine, 4-ethylcyclohexylamine, N-ethyl-1-adamantylamine, and 2-azabicyclo [2.2.2]octan-2~yl-amine.

27. A process as claimed in claim 1, wherein the amine is selected from the group consisting of:

N-aminopiperidine,

N-methyl-N-aminopiperidine,

N-ethyl-N-aminopiperdine,

N-propyl-N-aminopiperidine,

N-isopropyl-N-aminopiperidine,

N-butyl-N-amniopiperdine and

N-isobutyl-N-aminopiperidine.

28. A process as claimed in claim 1, wherein the amine is: N-aminopiperidine.

29. A process as claimed in claim 1 wherein, the quantity of amine used in method step c with respect to the quantity of compound of Formula I is in the range of about 1:1 to 1:20.

30. A process as claimed in claim 1, wherein the method step c is carried out at a temperature ranging from about 30° C. to the boiling point of the amine.

31. A process as claimed in claim 1, wherein the step of amidating is carried out for about 6 hours to 24 hours.

32. A process as claimed in claim 1, wherein the catalyst is a metal salt.

33. A process as claimed in claim 32, wherein the catalyst is at least one metal salt of a metal selected from the group consisting of manganese, calcium, zinc, cobalt, antimony, titanium and tin.

34. A process as claimed in claim 33, wherein the catalyst is at least one compound selected from the group consisting of manganese acetate, titanium acetate, calcium acetate, zinc acetate, antimony trioxide, antimony triacetate, cobalt acetate, tin oxide ,alkyl-titanate and alkoxytitanate.

35. A process as claimed in claim 34, wherein the catalyst is manganese acetate dihydrate.

36. A process as claimed in claim 1, wherein the proportion of catalyst with respect to the compound of Formula I is in the range of 30 ppm to about 100,000 ppm.

37. A process as claimed in claim 1, wherein the proportion of catalyst with respect to the compound of Formula I is in the range of 100 ppm to about 50,000 ppm.

38. A process as claimed in claim 1, wherein the nucleating agent is at least one agent selected from the group consisting of sodium acetate, sorbitol, sodium benzoate, sodium salicylate, nyacol, sodium sorbitrate, nano silica, tungsten trioxide, 3,5-di-i'-butyl-4-hydroxyphenyl propionic acid methyl ester, and ethylene acrylic acid sodium ionomer.

39. A process as claimed in claim 1, wherein the method step of separating excess amine includes the method step of separating the amine from the amidated mass by distillation.

40. A process as claimed in claim 1, wherein the step of separating the excess amine, includes an additional step of treating the amidated mass with a scavenging agent and further removing the traces of the amine and the scavenging agent by co-distillation.

41. A process as claimed in claim 40, wherein the scavenging agent is at least one scavenging agent selected from the group consisting of aromatic solvents, halogenated solvents, ethers and alcohols.

42. A process as claimed in claim 39, wherein the separated amine is reused.

43. A process as claimed in claim 1, wherein the method step of isolating compound of Formula IV from the second mass comprises:

i. treating the second mass with a water insoluble solvent and an aqueous alkali to form a first biphasic mixture with suspended insoluble particles;

ii. filtering the biphasic mixture to remove the insoluble particles to obtain a clear biphasic mixture;

iii. separating the compound of Formula IV in crude form, from the clear biphasic mixture; and iv. purifying the compound of Formula IV as a base or as an acid addition salt from the separated compound of Formula IV in crude form.

44. A process as claimed in claim 43, wherein the water insoluble solvent is selected from the group consisting of ethyl acetate, propyl acetate ,isopropyl acetate, butyl acetate, methyl ethyl ketone, methylisobutyl ketone, ethyl ether, diisopropyl ether, methyl t-butylether, MDC, EDC and chloroform.

45. A process as claimed in claim 43, wherein the aqueous alkali is at least one aqueous alkali selected from the group consisting of sodium carbonate, sodium bicarbonate , potassium carbonate, potassium bicarbonate, sodium hydroxide and potassium hydroxide.

46. A process as claimed in claim 43 wherein the proportion of, the water insoluble solvent with respect to the quantity of compound of Formula I is in the range of about 1:5 to about 1:50.

47. A process as claimed in claim 43 wherein the proportion of the aqueous alkali with respect to the quantity of the compound of Formula I is in the range of about 5 to about 20.

48. A process as claimed in claim 43, wherein the method step iii comprises:

i. separating the aqueous phase from the first biphasic mixture and retaining a first organic phase containing the compound of Formula IV in solution form;

ii. treating the first organic phase with an aqueous solution of a sequestering agent resulting in a second biphasic mixture in the reaction vessel , separating the aqueous phase from the second biphasic mixture and retaining a second organic phase containing the compound of Formula IV in solution form;

iii. treating the second organic phase with saturated aqueous sodium chloride solution to from a third biphasic mixture, iv. separating the aqueous phase from the third biphasic mixture and retaining a third organic phase containing the compound of Formula IV in solution form;

v. removing the solvent from the third organic phase and retaining the crude form of compound of Formula IV.

49. A process as claimed in claim 43 wherein the method step iv includes the method step of purifying the retained crude form of compound of Formula IV in the reaction vessel by treating it with water insoluble aliphatic solvent followed by isolation of the compound of Formula IV as a base by filtration.

50. A process as claimed in claim 49 wherein the aliphatic solvent is at least one solvent selected from a group of aliphatic solvents consisting of hexane, heptane and octane.

51. A process as claimed in claim 43 wherein the method step iv comprises:
adding a solvent selected from the group consisting of methanol, ethanol, isopropanol, acetone, and methylisobutylketone to the compound of Formula IV in crude from;
stirring the reaction mass to obtain a clear solution followed by addition of an acid; and
stirring and cooling the resulting slurry followed by filtration thereof to afford an acid addition salt of compound of Formula IV.

52. A process as claimed in claim 51, wherein the acid is selected from the group consisting of sulphuric acid, hydrochloric acid, hydrobromic acid, hydrofluoric acid, phosphoric acid and nitric acid, citric acid, oxalic acid, fumeric acid, maleic acid, tannic acid, tartaric acid, benzenesulfonic acid, methanesulfonic acid, paratoluenesulfonic acid, pamoic acid, stearic acid, and napthanoic acid.

53. A process as claimed in claim 43, wherein the method step iv comprises:
adding a solvent selected from the group consisting of methanol, ethanol, isopropanol, acetone, and methylisobutylketone to the compound of Formula IV in crude from;
stirring the reaction mass to obtain a clear solution followed by addition of 8-chloro-theophylline; and
stirring and cooling the resulting slurry followed by filtration thereof to afford a theoclate salt of compound of Formula IV.

54. A process as claimed in claim 16, wherein the step of separating the excess cyclizing agent includes an additional step of treating the first mass with a scavenging agent and further removing traces of the cyclizing agent and scavenging agent by co-distillation.

55. A process as claimed in claim 39, wherein the step of separating the excess amine, includes an additional step of treating the amidated mass with a scavenging agent and further removing the traces of the amine and the scavenging agent by co-distillation.

* * * * *